United States Patent
Dorn

(10) Patent No.: US 9,186,482 B2
(45) Date of Patent: Nov. 17, 2015

(54) ELONGATE MEDICAL DEVICE

(75) Inventor: Jürgen Dorn, Neulussheim (DE)

(73) Assignee: C. R. Bard, Inc., Tempe, AZ (US)

(*) Notice: Subject to any disclaimer, the term of this patent is extended or adjusted under 35 U.S.C. 154(b) by 663 days.

(21) Appl. No.: 12/742,655

(22) PCT Filed: Nov. 12, 2008

(86) PCT No.: PCT/EP2008/065385
§ 371 (c)(1),
(2), (4) Date: Aug. 23, 2010

(87) PCT Pub. No.: WO2009/062955
PCT Pub. Date: May 22, 2009

(65) Prior Publication Data
US 2010/0312325 A1  Dec. 9, 2010

(30) Foreign Application Priority Data

Nov. 12, 2007 (GB) .................................. 0722192.2

(51) Int. Cl.
| | | |
|---|---|---|
| *A61F 2/06* | (2013.01) | |
| *A61M 25/04* | (2006.01) | |
| *A61M 25/10* | (2013.01) | |
| *A61M 39/06* | (2006.01) | |
| *A61F 2/95* | (2013.01) | |

(52) U.S. Cl.
CPC ........... *A61M 25/04* (2013.01); *A61M 25/1011* (2013.01); *A61M 39/06* (2013.01); *A61F 2/95* (2013.01)

(58) Field of Classification Search
CPC ... A61F 2/95; A61F 2/966; A61F 2002/9517; A61M 25/10; A61M 2025/0004; A61M 2025/1052; A61B 17/0057; A61B 2017/00637
USPC ......... 606/108, 191, 194, 198, 200; 623/1.11, 623/1.12, 1.23
See application file for complete search history.

(56) References Cited

U.S. PATENT DOCUMENTS 4,846,791 A * 7/1989 Hattler et al. ................... 604/43
5,334,160 A 8/1994 Ellis
(Continued)

FOREIGN PATENT DOCUMENTS

| EP | 1210959 A2 | 6/2002 |
|---|---|---|
| EP | 1637092 A2 | 3/2006 |
| WO | WO 2006133959 A1 * | 12/2006 |

OTHER PUBLICATIONS

Mar. 12, 2009 International Search Report in PCT Application No. PCT/EP2008/065385 Filed on Nov. 12, 2008.
(Continued)

*Primary Examiner* — Katherine M Shi
(74) *Attorney, Agent, or Firm* — Buchalter Nemer

(57) ABSTRACT

This invention relates to an elongate medical device, with a distal end to be advanced into the body of a patient and then withdrawn from the body, and an elongate shaft connecting the distal end with a proximal end that remains outside the body, the shaft extending in use through a hole in the skin of the body characterized by a slider, captivated on a portion of the length of the shaft, which is capable of lining the said hole, as the shaft is advanced and withdrawn relative to said hole and the slider in the hole, said slider having a maximum outer diameter that is substantially the same as or less than a maximum outer diameter of the distal end.

8 Claims, 2 Drawing Sheets

(56) References Cited

U.S. PATENT DOCUMENTS

| | | | |
|---|---|---|---|
| 5,415,664 A * | 5/1995 | Pinchuk | 623/1.11 |
| 5,634,928 A * | 6/1997 | Fischell et al. | 623/1.11 |
| 5,772,669 A * | 6/1998 | Vrba | 623/1.11 |
| 5,980,533 A * | 11/1999 | Holman | 623/1.11 |
| 6,391,050 B1 * | 5/2002 | Broome | 623/1.11 |
| 2003/0009128 A1 | 1/2003 | Ackerman et al. | |
| 2003/0023267 A1 * | 1/2003 | Ginn | 606/213 |
| 2005/0010247 A1 * | 1/2005 | Kusleika et al. | 606/200 |
| 2005/0085856 A1 * | 4/2005 | Ginn | 606/213 |
| 2006/0030884 A1 * | 2/2006 | Yeung et al. | 606/232 |
| 2006/0282148 A1 * | 12/2006 | Hammersmark et al. | 623/1.11 |
| 2007/0050006 A1 * | 3/2007 | Lavelle | 623/1.11 |
| 2008/0071345 A1 * | 3/2008 | Hammersmark et al. | 623/1.11 |

OTHER PUBLICATIONS

Mar. 12, 2009 PCT Written Opinion for Application No. PCT/EP2008/065385 Filed on Nov. 12, 2008.

Dec. 18, 2009 International Preliminary Report on Patentability for Application No. PCT/EP2008/065385 Filed on Nov. 12, 2008.

* cited by examiner

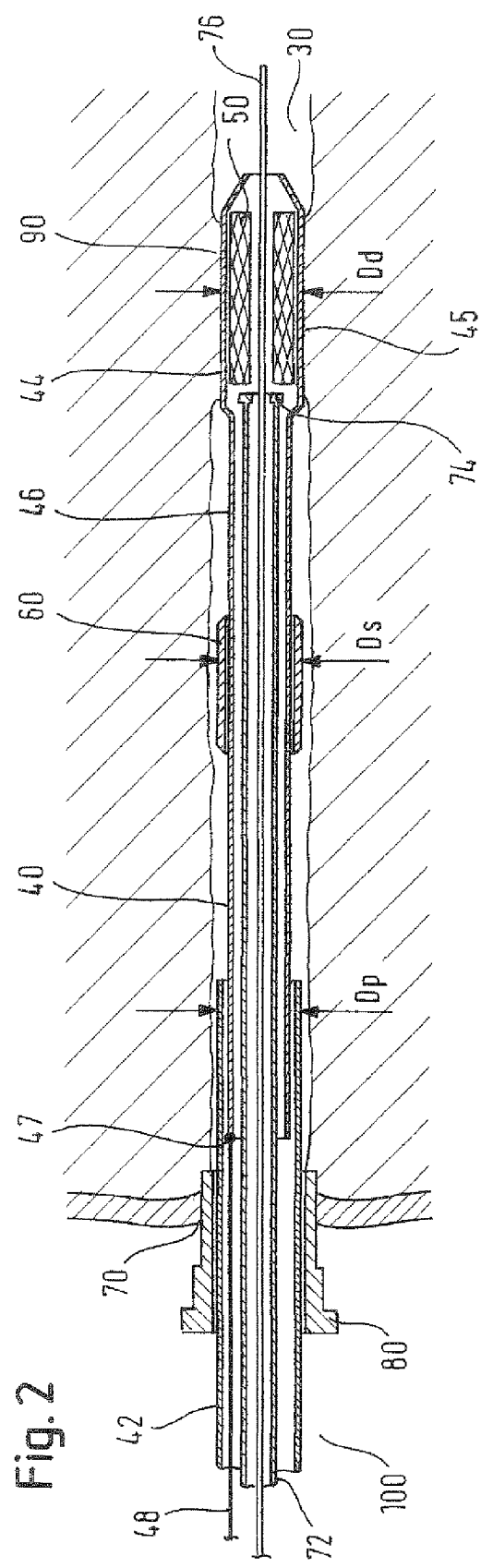
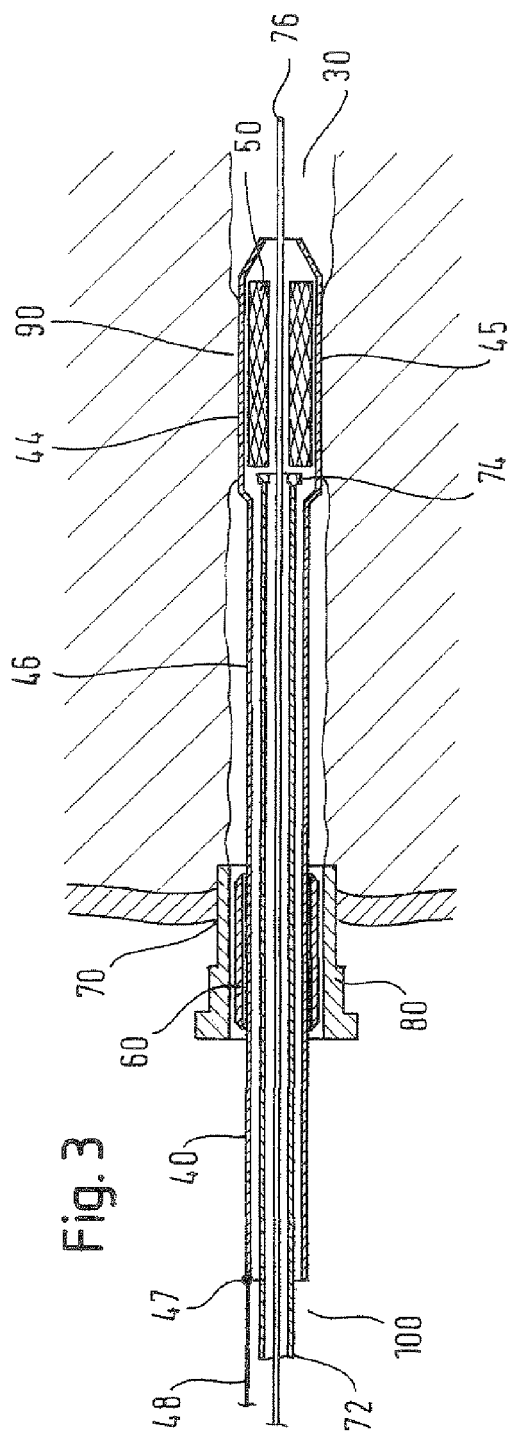

ELONGATE MEDICAL DEVICE

PRIORITY

This application is a U.S. national stage application under 35 USC §371 of International Application No. PCT/EP2008/065385, filed Nov. 12, 2008, claiming priority to United Kingdom Patent Application No. 0722192.2, filed Nov. 12, 2007, each of which is incorporated by reference in its entirety into this application.

TECHNICAL FIELD

This invention relates to an elongate medical device, with a distal end to be advanced into the body of a patient and then withdrawn from the body, and an elongate shaft connecting the distal end with a proximal end that remains outside the body, the shaft extending in use through a hole in the skin of the body.

BACKGROUND PRIOR ART

A catheter serving as a stent delivery system is just one example of a medical device with a distal end that is advanced into the body through a percutaneous puncture. The distal end advances in the body transluminally. Often, the lumen is part of the cardiovascular system, but not necessarily. In one very common procedure, known as the Seldinger technique, catheters are introduced into the cardiovascular system through a puncture point in the thigh of the patient.

As stent delivery catheter devices become more sophisticated, they have become more compact, in cross-sectional areas. The normal unit of dimension to designate cross-sectional areas is the unit of length called "French" which is ⅓ of a millimeter. Thus, a "Six-French" catheter has an outside diameter of two millimeters.

With increasing diameter, the demands on tissue at the point of entry to the body, and the risk of leakage of blood at that entry point, tend to increase. Typically, a catheter is introduced at the point of entry of the body through an introducer sleeve which extends from outside the body, through the puncture point, into the lumen of interest, to provide a path along which the distal end of the catheter can advance through the percutaneous puncture and into the desired lumen. However, the provision of such an introducer sleeve increases the diameter required, at the point of entry to the body. Self-evidently, doing without any introducer sleeve would be one way to reduce the total diameter needed, at the point of entry. Indeed, some doctors are responding to tissue difficulties at the point of entry by performing the catheter introduction without any introducer sleeve. While this reduces the total diameter requirement, it brings disadvantages, specifically, that the abluminal surface of the catheter moves longitudinally, proximally and distally, against the bodily tissue at the point of entry, tending to increase the likelihood of loss of blood at that entry point.

An elongate medical device that is advanced transluminally within the body of a patient usually has a distal end that is to perform some sort of medically advantageous function within the body, such as deploying a stent. Normally, the shaft serves as a link between the proximal and distal ends of the device but does not have to perform a medical procedure in its own right, so it can be slimmer. The present invention is particularly adapted to medical devices in which the maximum cross-section of the distal end of the device is greater than the maximum cross-sectional area of the shaft portion. For examples of medical devices featuring a distal tip that is somewhat thicker than its shaft, reference is made to EP-A-1025813 and U.S. Pat. No. 5,772,669.

In order to reduce the leakage of blood through the entry point, often referred to as "backbleed", the use of an additional sleeve placed around the catheter shaft has been suggested in U.S. Pat. No. 5,203,774. This sleeve is slidably arranged on the catheter shaft so that it can be axially displaced with respect to the catheter and has a distal end for being introduced into the inner lumen of an introducer sleeve. A flange with a diameter that is larger than that of said distal end is provided at a proximal end of the sleeve. The flange engages over the edges of the introducer sleeve so as to prevent the sleeve from being axially displaced. Such an arrangement allows the catheter shaft to be freely advanced and retracted with respect to the sleeve partly positioned in the introducer sleeve but reduces backbleed that, in the absence of the sleeve, may occur through the gap between the inner lumen of the introducer sleeve and the catheter shaft. A similar sleeve configuration is also disclosed in U.S. Pat. No. 5,836,306 and U.S. Pat. No. 5,334,160.

The sleeve arrangements described in the above-referenced documents ought to reduce the occurrence of backbleed, in particular with respect to the length of constant external diameter of the shaft of the catheter as it is introduced into a patient's body. These sleeves are configured to be disposed within a proximal portion of an introducer sleeve and prevented from any further distal movement in an axial direction of the catheter shaft by a proximal sleeve portion, such as a flange, that has an outer diameter larger than the inner diameter of the proximal introducer sleeve portion. Hence, the length along which the medical device can be introduced into a patient's body is limited to the length of the catheter shaft which can advance through the sleeve. Specifically, if the catheter were to have a thicker proximal shaft portion which has an outer diameter larger than the inner diameter of the sleeve, then such a proximal portion would have to remain at all times proximal of the backbleed-preventing introducer sleeve.

In peripheral vascular procedures, the distance between the point of bodily entry and the site of surgical treatment within the body can widely vary and may not be known precisely in advance of the procedure.

FR-A-2 625 897 discloses a conically shaped plug element that is slidably disposed around the tube of a medical probe. After the probe has been introduced into the blood vessel of a patient, the plug element is arranged and fixed within the entry point of the vessel so as to tightly seal it. When inserted in the entry point, the plug element exerts a pressure on the probe tube that is sufficient to prevent it from moving in an axial direction of the probe. In this way, the probe is immobilised in a desired position with respect to the blood vessel.

SUMMARY OF THE INVENTION

According to the present invention there is provided an elongate medical device as identified above, and characterised by a slider, captivated on a portion of the length of the shaft, which is capable of lining the said percutaneous hole as the shaft is advanced and withdrawn relative to said hole and to the slider in the hole, said slider having a maximum outer diameter that is substantially the same as or less than a maximum outer diameter of the distal end of the medical device.

It will be appreciated that a medical device provided with the slider of the invention can function without an introducer sleeve. The distal end of the device is advanced distally through the hole that is the point of entry into the body and then, once the distal end is through the hole, the slider can be positioned within the hole, to line the hole. After that, the shaft of the medical device can be advanced distally through the lined hole, with relative sliding motion between the shaft portion and the luminal surface of the slider, while the abluminal surface of the slider remains motionless on the bodily tissue defining the hole that is the entry point in the body. It will be appreciated that the presence of the slider in the hole is useful for restricting or inhibiting flow of blood from within the body, through the hole, to locations outside the body.

Further, it will be appreciated that the presence of the slider in the hole can reduce the degree of trauma imposed on the tissue surrounding the hole, not only because that tissue is no longer subject to the sliding motion over the tissue of the advancing or withdrawing shaft portion but also because the tissue need not be stretched further, in order to incorporate an introducer sleeve that has a diameter necessarily greater than the maximum diameter of the distal end of the elongate medical device.

It will further be appreciated that medical devices in accordance with the present invention can easily be designed in such a way as to be compatible with an introducer sleeve. This is advantageous for it gives the decision-making medical practitioner the choice of employing an introducer sleeve, or of choosing to do without one, without having to switch from one elongate medical device to another.

Furthermore, the slider of the present invention has a maximum outer diameter that is substantially the same as or less than a maximum outer diameter of the distal end. Thus, the slider can be advanced through the entry point and beyond, into the accessed lumen of the patient's body, whether or not an introducer sleeve is used. In this way, the length of an introduction path of the medical device is not limited by the presence of the slider. Hence, the same device can be used for different procedures with varying distances from the entry point to the area to be treated within the body, which is particularly advantageous in peripheral vascular procedures as explained above.

The shaft of the medical device may have a proximal portion with a diameter that is greater than the diameter of the shaft portion other than the proximal portion. In particular, the proximal portion may have a maximum outer diameter that is substantially the same as or less than the maximum outer diameter of the distal end. In this case, depending upon the distance between the point of entry and the point of surgical treatment, the proximal shaft portion can be proximal of the entry point into a patient's body (with the sleeve lining the entry point or introducer) or bridging the entry point (in which case the sleeve is wholly distal of the entry point and any introducer element through which the medical device extends at the point of entry)

Of particular interest for releasing self-expanding stents are catheters that include a pull wire, in a lumen in the shaft of the catheter, that is pulled proximally progressively to release the stent from within a confining sheath, starting at the distal end of the stent. During such release, the wire moves proximally through the catheter introducer lumen, but not the abluminal surface of the stent delivery catheter.

One envisages in a preferred embodiment a slider that has an outside diameter not greater than the maximum diameter of the distal end of the elongate medical device, yet larger than the outside diameter of a shaft portion on which the slider is slidable. We think that a slider length in a range of from 1 cm to 4 cm will be attractive to medical practitioners and, currently, a slider length of around 15 mm is thought to be particularly suitable. Most of the axial length of the slider, in preferred embodiments, will have a circular cross-section cylindrical abluminal surface, flanked at a proximal and distal end by tapered portions, tapering inwardly in order to minimise tissue trauma when the slider is brought into coincidence with the entry point hole in bodily tissue.

The reader will appreciate that the slider should slide freely on the shaft portion and that this process might be assisted by providing the luminal surface (bore surface) of the slider with a lubricious coating. As to the abluminal surface of the slider, skilled readers will have common general knowledge what sorts of surfaces are best adapted for residing in entry point punctures. Those engineers responsible, for example, for designing and constructing introducer sleeves will have considerable experience what sorts of surfaces to adopt. One imagines a range of coatings might be useful for the abluminal surface of the slider, even perhaps including a blood clotting agent, further to reduce flow of blood over the slider surface, outwardly of the body.

For a better understanding of the present invention, and to show more clearly how the same may be carried into effect, reference will now be made, by way of example, to the attached drawings, in which FIG. 1 is a reproduction of FIG. 1 of EP-A-125813, modified to show a slider captivated on a shaft portion of the stent introducer catheter showed in the drawing, and FIGS. 2 and 3 show a stent introducer catheter such as that of FIG. 1 that is inserted into a patient's body.

The drawing is a simplified perspective view of a stent delivery apparatus 1, which comprises inner and outer coaxial tubes. The inner catheter 12 extends along the length of an outer shaft portion 40, from a proximal end 42 to a distal end 45. The distal end 45 of the shaft 40 includes an enlarged section 44 that has a larger outside diameter than the outside diameter of the shaft 40. Enlarged section 44 houses (not shown) a stent 50 that is to be delivered by the device. The device is an "over-the-wire" device that advances along a guidewire 76.

Mounted on the shaft 40 is a slider 60, to be a relatively tight sliding fit on the outside surface of the shaft 40. It has a length of 15 mm and is basically an annulus 62 of circular cross-section cylindrical form with a diameter of typically 7 French and the ends 64, 66 of the cylinder are tapered for reduction of the amount of trauma caused to tissue if the slider is advanced through the percutaneous entry point for the stent delivery catheter system into the body.

In the illustrated embodiment, the shaft portion on which the slider may slide is a portion running the full length of the shaft, from the distal end 45 to a proximal hub 52. In other embodiments, however, such as that shown in FIGS. 2 and 3, the shaft portion on which the slider slides might constitute only a relatively small portion of the total length of the medical device, for example, corresponding to that part of the length of the shaft which will reside in the entry point hole while the medical device is actually performing a medical procedure within the body.

While the illustrated embodiment has a smooth constant diameter cylindrical abluminal surface, other embodiments of slider might have other abluminal surface topographies including, for example, axial ridges or grooves, perhaps to retain desired fluid coating materials, or transverse ridges or grooves, perhaps to further limit passage of blood between the slider and the surrounding bodily tissue. Similarly, on the luminal surface of the slider, one can envisage whatever topography best achieves the sliding sealing effect desired. In any event, it is expected that the medical practitioner will need manually to manipulate the slider into exactly that location within the entry point hole that the doctor thinks is optimal. For that, the abluminal surface of the slider, accessible from the proximal end of the slider, would need to be compatible with some sort of grip imposed on the slider by the medical practitioner. However, if the medical device is to be compatible with use through an introducer sleeve, then whatever means are provided at the proximal end of the slider to facilitate gripping by the doctor, this should not conflict with passage of the slider through the introducer sleeve, both distally and proximally. In particular, the need to withdraw the slider proximally through the introducer sleeve, from a position where it is entirely distally beyond the distal-most point of the introducer sleeve, as shown in FIG. 2, ought not to be overlooked. One envisages that the distal end of the introducer sleeve would abut the proximal end of the slider while the shaft of the medical device is being withdrawn proximally through the introducer sleeve, and only when the distal end of the slider is butted up against the larger diameter distal end portion of the elongate device would the inwardly tapered proximal end of the slider advance proximally into the interior of the introducer sleeve.

FIGS. 2 and 3 show cross-sectional views of a part of a stent introducer catheter 100 that has been introduced into the lumen of a blood vessel 30 through an entry point hole 70 in the body of a patient with the help of an introducer sleeve 80. The configuration of the proximal part of the stent introducer catheter 100, which is not shown in FIGS. 2 and 3, is comparable to that of the stent introducer catheter 1 shown in FIG. 1 and skilled readers are in any case familiar with the details of construction and operation of the actuator devices that are located at the proximal end of a stent delivery catheter. Furthermore, the same reference signs as in FIG. 1 will be used for identical and equivalent elements.

The stent introducer catheter 100 has a distal end 45 with a maximum outer diameter Dd that houses a self-expanding stent 50. The distal end 45 is connected with a proximal end (not shown) of the device by a shaft portion 40 having a proximal portion 42 with a larger diameter Dp and a distal portion 46 with a smaller diameter. A slider 60 with an outer diameter Ds that has substantially the same configuration as that shown in FIG. 1 is slidably disposed around the distal shaft portion 46 so that it can freely move in an axial direction between the proximal shaft portion 42 and the distal end 45 of the catheter 100. The outer diameters of the proximal shaft portion 42, the slider 60 and the distal end 45, Dp, Ds and Dd are substantially identical.

The stent introducer catheter 100 further comprises a pusher element 72 that is disposed within an inner lumen of the shaft portion 40. The pusher element 72 has a distal end 74 that abuts the proximal end of the stent 50 during stent deployment thus holding the stent in its axial position. The distal shaft portion 46 is at its proximal end 47 connected to a pull wire 48 that runs inside the proximal shaft portion 42 all the way to the proximal end (not shown) of the stent introducer catheter 100.

FIGS. 2 and 3 both show a configuration, after advance of the stent to the site of stenting but prior to deployment of the stent, in which the stent introducer catheter 100 has already been introduced into a patient's blood vessel 30 such that its distal end 45 is positioned at a stenosis 90. In the case of FIG. 2, the stenosis 90 is spaced from the entry point hole 70 by a distance close to the full length of the catheter shaft. Otherwise, in the case of FIG. 3, the stenosis 90 lies closer to the entry point hole 70. Since the outer diameters Dp, Ds and Dd of the proximal shaft portion 42, the slider 60 and the distal end 45 are all substantially identical and all a snug fit with the bore of the introducer sleeve 80, the stent introducer catheter 100 can be used, substantially free of backbleeding, for both cases without the requirement of any modifications to the device 100. In this way, the stent delivery system can be used, unmodified, regardless how near or far the stenosis is from the point of percutaneous entry of the catheter into the bodily lumen.

Next, the operation of the stent introducer catheter 100 for deploying the stent 50 is described. When the distal end 45 is arranged in the blood vessel 30 in such a way that the stent 50 is in a desired position at the site of the stenosis 90, as shown in FIGS. 2 and 3, the medical practitioner causes the pull wire 48 to be pulled proximally at the proximal end of the stent introducer catheter 100. This pulling force causes a proximal movement of the distal shaft portion 46 and consequently also the enlarged section 44 relative to the pusher element 72 which is free from axial translation of movement during the deployment procedure. Since the stent 50 is securely held in its position by abutment on the distal end 74 of the pusher element 72, the enlarged section 44, which is an outer sheath holding the stent 50 in its compressed state, is retracted from the abluminal surface of the stent 50, allowing the stent 50 to radially expand. Once the stent 50 is fully deployed, the stent introducer catheter 100 can be removed from the patient's body through the introducer sleeve 80.

In the case shown in FIG. 2, the proximal shaft portion 42, which is stationary during stent deployment, is positioned within the introducer sleeve 80, while in the case shown in FIG. 3 the slider 60 is arranged in this position. Importantly, in both cases, there is no contact between the inner surface of the introducer sleeve 80 and any moving part of the stent introducer catheter 100, such as the distal shaft portion 46, thereby greatly reducing friction during the stent deployment process. The inventor has found out that such friction can lead to serious complications during the medical procedure. In particular, if the distal shaft portion 46 because of contact with the inner surface of the introducer sleeve 80 is prevented by friction between the shaft and the introducer is prevented from sliding smoothly proximally through the point of percutaneous entry while at the same time a relative movement of the distal shaft portion 46 and the pusher element 72 is effected by the medical practitioner by proximally pulling the pull wire 48, the stent 50 can be pushed forward along the bodily lumen in an axial direction, away from its desired location. Any such behaviour could lead to dangerous inaccuracies in the placement of the stent 50. With the stent introducer catheter 100 of the present embodiment such complications can be reliably avoided, enabling stent deployment with a high degree of accuracy of placement, independent on whether the stenosis 90 to be treated is located close to or far away from the entry point hole 70, and all using just one introducer catheter long enough to reach stenting sites furthest away from the point of entry of the delivery system.

If no introducer sleeve 80 is used and the stent introducer catheter 100 is introduced directly through the entry point hole 70, the configuration of the present embodiment has the additional advantage that any movement of the distal shaft portion 46 against the bodily tissue at the point of entry is avoided, thus not only any tendency to backbleed but also reducing trauma to bodily tissue at the point of entry.

Although the illustrated embodiments are of a stent delivery system catheter, an over-the-wire catheter for a self-expanding stent, the reader will appreciate that the slider idea of the present invention is applicable to other sorts of catheters and indeed to medical devices introduced into the body that are strictly not correctly identified as a catheter. Whereas the slider invention might still be useful at diameters of 6 French and below, it is thought that the slider idea begins to become particularly interesting for medical practitioners, as soon as the overall diameter of the device to be introduced into the body begins to increase substantially above 7 French.

In general, skilled readers will appreciate that the invention has wide application beyond the specific device shown in the drawing, and that wide variation is possible in the features of construction and selection of materials in the slider of the invention. Readers will bring to bare on the matter their background and experience in the field of catheter introducer sleeves and transluminal stent delivery systems.

FIG. 1. is a perspective view of a medical device.

FIG. 2 is a section view along the longitudinal axis of a medical device.

FIG. 3 is a section view along the longitudinal axis of another medical device.

Figure 1:
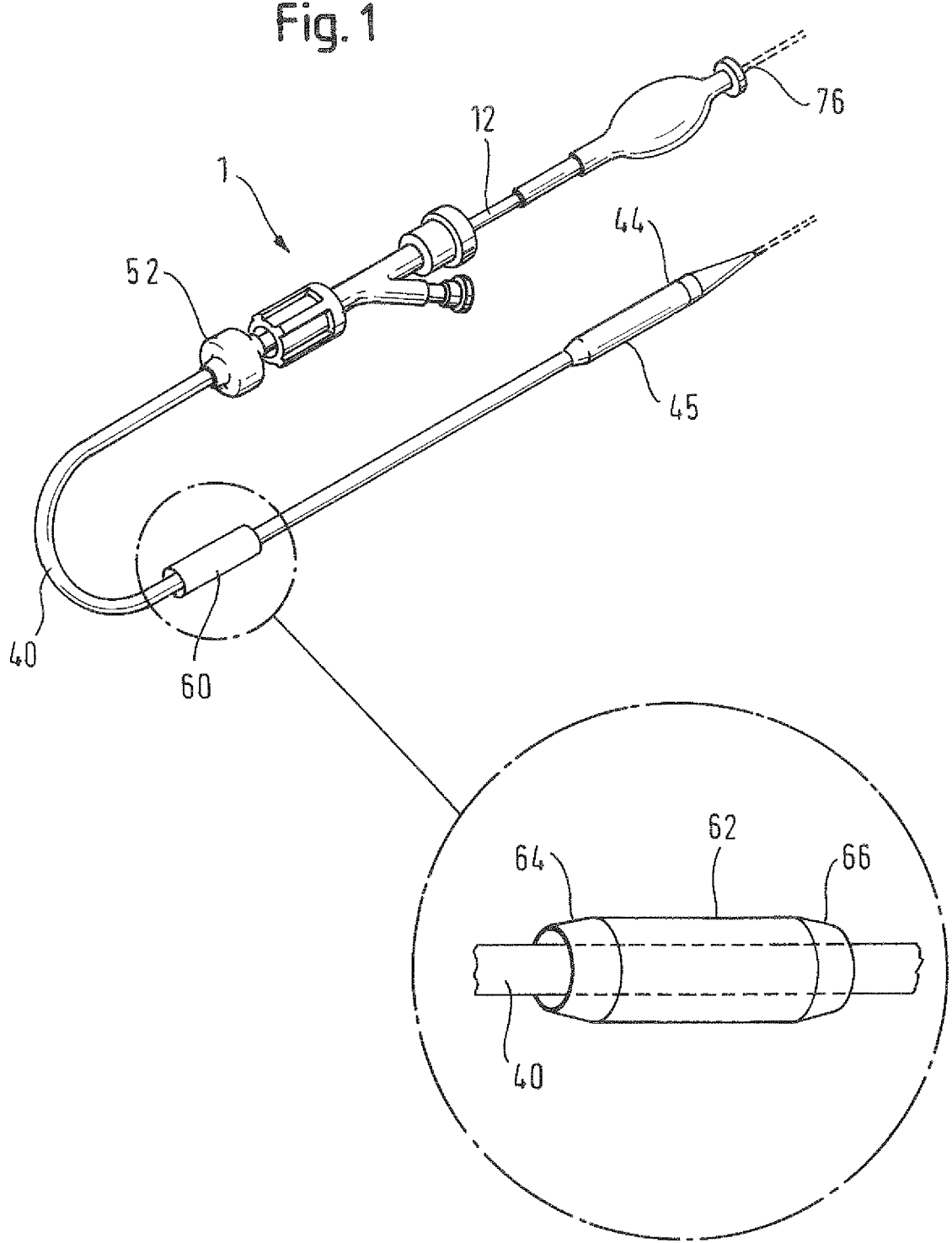

The invention claimed is:

1. An elongate medical device, comprising:
   an elongate shaft distal end to be advanced into the body of a patient and then withdrawn from the body, a portion of which remains outside the body, connecting the shaft distal end with a shaft proximal end, the shaft extending in use through a hole in the skin of the body, a stent covered by the shaft distal end;
   and
   a slider captivated on a portion of the length of the shaft such that the shaft distal end is distal a slider distal end and the shaft proximal end is proximal a slider proximal end and configured to line the hole and remain in the hole as the shaft is advanced and withdrawn relative to the hole and the slider in the hole, the slider having a maximum outer diameter that is substantially the same as or less than maximum outer diameter of the shaft distal end, and
   wherein
   the distal end includes a pull-back sheath,
   and
   the shaft portion cross-section includes a pull wire for pulling the pull-back sheath proximally relative to the distal end.

2. An elongate medical device, comprising:
   an elongate shaft distal end to be advanced into the body of a patient and then withdrawn from the body, a portion of which remains outside the body, connecting the shaft distal end with a shaft proximal end, the shaft extending in use through a hole in the skin of the body, a stent covered by the shaft distal end;
   and
   a slider captivated on a portion of the length of the shaft such that the shaft distal end is distal a slider distal end and the shaft proximal end is proximal a slider proximal end and configured to line the hole and remain in the hole as the shaft is advanced and withdrawn relative to the hole and the slider in the hole, the slider having a maximum outer diameter that is substantially the same as or less than maximum outer diameter of the shaft distal end,
   wherein the shaft has a proximal portion with an abluminal surface that has a diameter that is greater than a diameter of that portion of the shaft that is distal of the shaft proximal portion and proximal of a shaft distal portion and
      wherein the shaft proximal portion has a maximum outer diameter that is substantially the same as a maximum outer diameter of the sheath distal end.

3. The device according to claim 2, wherein said abluminal surface of the proximal portion of the shaft does not move proximally, relative to the stent, during deployment of the stent.

4. The device according to claim 2, wherein the slider has a maximum outer diameter that is substantially the same as the maximum outer diameter of the shaft proximal portion.

5. An elongate medical device comprising:
   an elongate shaft having a distal end including a pull-back sheath to be advanced into the body of a patient and then withdrawn from the body, the shaft that remains outside the body enclosing a lumen connecting the shaft distal end with a shaft proximal end, the shaft extending in use through a hole in the skin of the body, a stent covered by the shaft distal end;
   and
   a slider captivated on a portion of the length of the shaft such that the shaft distal end is distal a slider distal end and the shaft proximal end is proximal a slider proximal end and configured to line the hole and remain in the hole as the shaft is advanced and withdrawn relative to the hole and the slider in the hole, the slider having a maximum outer diameter that is substantially the same as or less than maximum outer diameter of the sheath distal end,
   wherein the shaft portion includes a pull wire for pulling the pull-back sheath proximally.

6. An elongate medical device comprising:
   a shaft distal end to be advanced into the body of a patient and then withdrawn from the body, an elongate shaft that remains outside the body enclosing a lumen connecting the shaft distal end with a shaft proximal end, the shaft extending in use through a hole in the skin of the body, a stent covered by the shaft distal end;
   and
   a slider captivated on a portion of the length of the shaft such that the shaft distal end is distal a slider distal end and the shaft proximal end is proximal a slider proximal end and configured to line the hole and remain in the hole as the shaft is advanced and withdrawn relative to the hole and the slider in the hole, the slider having a maximum outer diameter that is substantially the same as or less than maximum outer diameter of the shaft distal end,
   wherein
   the shaft has a proximal portion with an abluminal surface that has a diameter that is greater than a diameter of that portion of the shaft that is distal of the shaft proximal portion and proximal of a shaft distal portion,
   and
   the shaft proximal portion has a maximum outer diameter that is substantially the same as a maximum outer diameter of the shaft distal end.

7. The device according to claim 6 wherein the abluminal surface of the proximal portion of the shaft does not move proximally, relative to the stent, during deployment of the stent.

8. The device according to claim 6 wherein the slider has a maximum outer diameter that is substantially the same as the maximum outer diameter of the shaft proximal portion.

\* \* \* \* \*